United States Patent [19]

Pols

[11] 4,178,703
[45] Dec. 18, 1979

[54] SHOE TO BE WORN OVER CAST

[76] Inventor: Sidney Pols, c/o E. J. Sabel & Co., Benson E. Bldg., P.O. Box 644, Jenkintown, Pa. 19046

[21] Appl. No.: 909,016

[22] Filed: May 24, 1978

[51] Int. Cl.² ............................................. A43B 21/00
[52] U.S. Cl. ............................................ 36/110; 36/105
[58] Field of Search .................... 36/110, 81, 69, 71, 36/103, 104, 105, 8.2

[56] References Cited
U.S. PATENT DOCUMENTS

| 2,198,338 | 4/1940 | Greider | 36/104 |
| 2,409,813 | 10/1946 | Timson | 36/105 |
| 3,566,487 | 3/1971 | Beightol | 36/110 |
| 3,905,135 | 9/1975 | Debusk | 36/110 |

Primary Examiner—Patrick D. Lawson
Attorney, Agent, or Firm—Zachary T. Wobensmith, 2nd; Zachary T. Wobensmith, III

[57] ABSTRACT

A removable shoe to be worn over a cast that extends over the foot of a person, which shoe provides protection to the cast and by use of a heel wedge internal or external to the shoe provides an improved walking action.

4 Claims, 6 Drawing Figures

SHOE TO BE WORN OVER CAST

BACKGROUND OF THE INVENTION

1. Field of the Invention

This invention relates to a removable shoe to be worn over a cast.

2. Description of the Prior Art

The modern medical view with persons who have to wear casts on a foot, or on the leg and foot, has been to encourage such person to exercise by walking consistent with the nature of the injury. Most casts in use are made of a plaster of paris material which is not highly resistant to moisture, and since many casts expose the toes and sometimes a portion of the heel to the elements can easily deteriorate. A shoe that can be worn over the cast for protection and cast support is most desirable and until my invention no wholly satisfactory shoe has been available. Such a shoe should be easy to put on and take off and should assist the wearer in walking.

Shoes have been provided for wearing over casts and one such example is shown in the U.S. Patent to R. F. Larkin, U.S. Pat. No. 2,614,340 which shows a walking cast shoe which extends over the toes and rearwards about ⅝ the length of the foot, with the heel of the cast exposed and the weight of the cast supported on a yoke 6 which contacts the ground outside the shoe thereby transmitting the ground contact shock directly to the cast, which in addition is not supported along the length of its bottom.

Various shoe constructions have been proposed which utilize a wedge type of construction for the sole and heel such as is shown in the U.S. patent to Edmonds, U.S. Pat. No. 3,555,706, which shows athletic footwear, particularly basketball shoes, which includes an outer flat bottom sole 2 and an inner sole 3 of tapered construction but which shoe is not suitable for use with a cast.

Another example of footwear with wedge construction is shown in the U.S. Patent to Maling, U.S. Pat. No. 2,150,385, which illustrates a shoe construction having a built up heel inside of the shoe, which built up heel is composed of resilient materials and only extends to the arch of the foot.

Another example of footwear with an inner heel wedge inside the shoe is illustrated in the U.S. Patent to Reeves, U.S. Pat. No. 2,262,371 which shows a heel wedge member 10 inside a shoe which is shaped to conform to the rear half of the bottom of a shoe.

Another example of wedge construction footwear is shown in the U.S. Patent to Ogasawara, U.S. Pat. No. 3,006,083, which illustrates a ladies wedge style shoe which includes a wedge under the rear half of the foot which extends forward to the arch but is not suitable for use with a cast.

Another example of the wedge type of shoe construction is shown in the U.S. Patent to Epstein, U.S. Pat. No. 3,810,318, which illustrates a shoe to aid children to walk and which has an inner sole with extension and raised rear portion which extends about one half the length of the sole.

None of the available structures provide a readily removable shoe to be worn on a cast which provides support for the entire bottom of the cast and aids the wearer to walk.

SUMMARY OF THE INVENTION

This invention relates to a readily removable shoe to be worn over a cast which includes a heel wedge which is located either internally or externally of the shoe, and which aids the wearer to walk.

The principal object of the invention is to provide a shoe to be worn over a cast which provides complete support to the cast for walking and which affords a high degree of protection to the cast.

A further object of the invention is to provide a shoe to be worn over a cast which is readily removable.

A further object of the invention is to provide a shoe to be worn over a cast which is simple and inexpensive to construct but sturdy and reliable in use.

A further object of the invention is to provide a shoe to be worn over a cast which aids the wearer to walk.

Other objects and advantageous features of the invention will be apparent from the description and claims.

DESCRIPTION OF THE DRAWINGS

The nature and characteristic features of the invention will be more readily understood from the following description taken in connection with the accompanying drawings forming part hereof in which.

It should, of course, be understood that the description and drawings herein are illustrative merely and that various modifications and changes can be made in the structure disclosed without departing from the spirit of the invention.

Like numerals refer to like parts throughout the several views.

DESCRIPTION OF THE PREFERRED EMBODIMENTS

Figure 1:
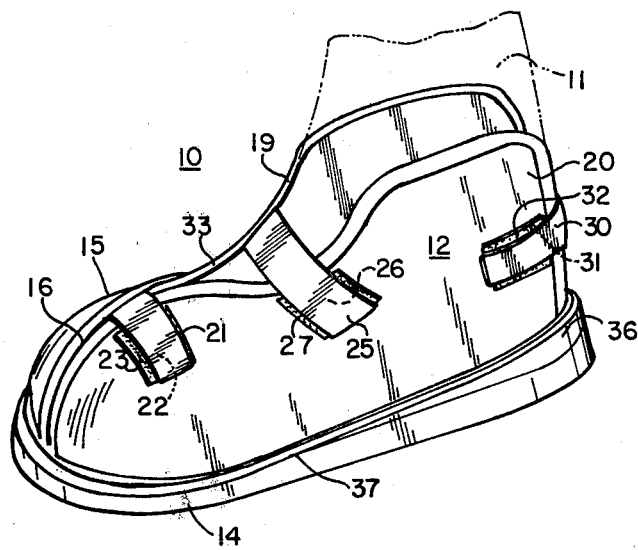
FIG. 1 is a perspective view of one embodiment of the shoe of the invention in place on the cast of a wearer.
Figure 2:
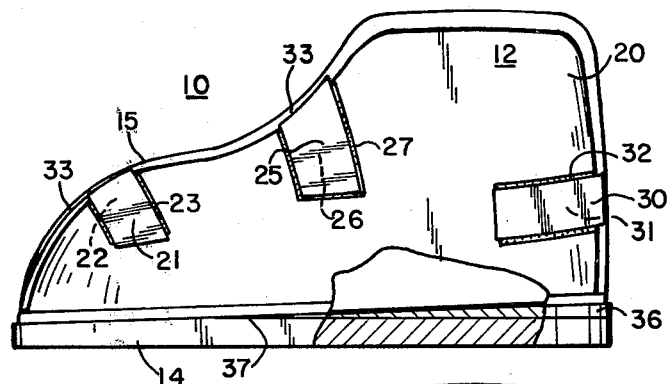
FIG. 2 is a side elevational view of the shoe of FIG. 1 with a portion removed to show the inner construction.

Referring now more particularly to the drawings and FIGS. 1 and 2 thereof, one embodiment of shoe 10 is illustrated with a cast 11 shown in phantom therein. The shoe 10 consists of an upper 12 and a sole 14 attached to the upper 12. The upper 12 is shown as being of split construction with a toe portion 15 which is split from point 16 into side halves 19 and 20 which respectively are disposed on either side of the cast 11. The upper halves 19 and 20 are joined together from point 16 down to the sole 14 in the front toe portion 15 by a line of stitching (not shown) and detachably secured together at the toe by a strap 21 secured to upper half 19 with a strip of thistle cloth 22 on one side of well known type such as "Velcro" and which is shown as engaged with a complementary strip of thistle cloth 23 on the upper half 20.

A second strap 25 is provided attached to upper half 19, with a strip of thistle cloth 26 on one side which is shown as engaged with a complemental strip of thistle cloth 27 on upper half 20.

A third strap 30 is provided which extends around the rear of the cast 11 at the ankle with a strip of thistle cloth 31 on one side for engagement with a complemental strip of thistle cloth 32 on the upper half 20.

The upper halves 19 and 20 along their meeting edge may be provided with strips of cloth edging 33 along their facing edges and can be fabricated of any suitable type of reinforced material such as a vinyl backed cloth of well known type.

The sole 11 is fastened to the upper 10 by any suitable means such as lines of stitching (not shown) and a film of adhesive of well known type. The sole 14 is preferably formed of a resilient spongy material and has a flat bottom surface 35 which may have a non-slip pattern thereon (not shown) of well known type. An inner heel wedge 36 is shown interposed between the sole 14 and the upper 11 which is thicker at the rearmost portion of the heel and tapers down to a knife like edge 37 on a vertical line with the second strap 25.

Figure 3:
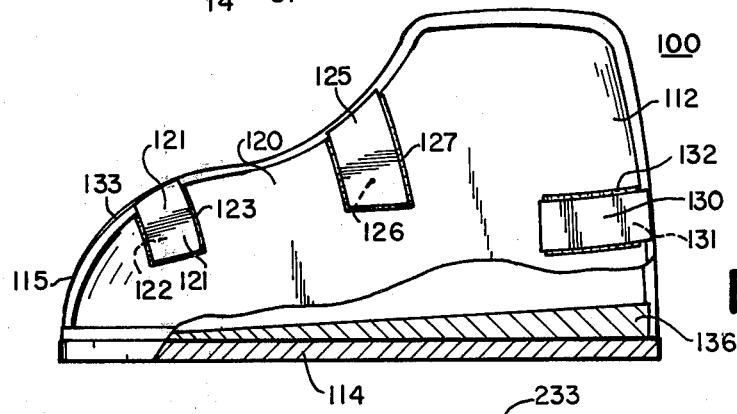
FIG. 3 is a side elevational view of another embodiment of the shoe of the invention with a portion removed to show the internal construction.
Figure 5:
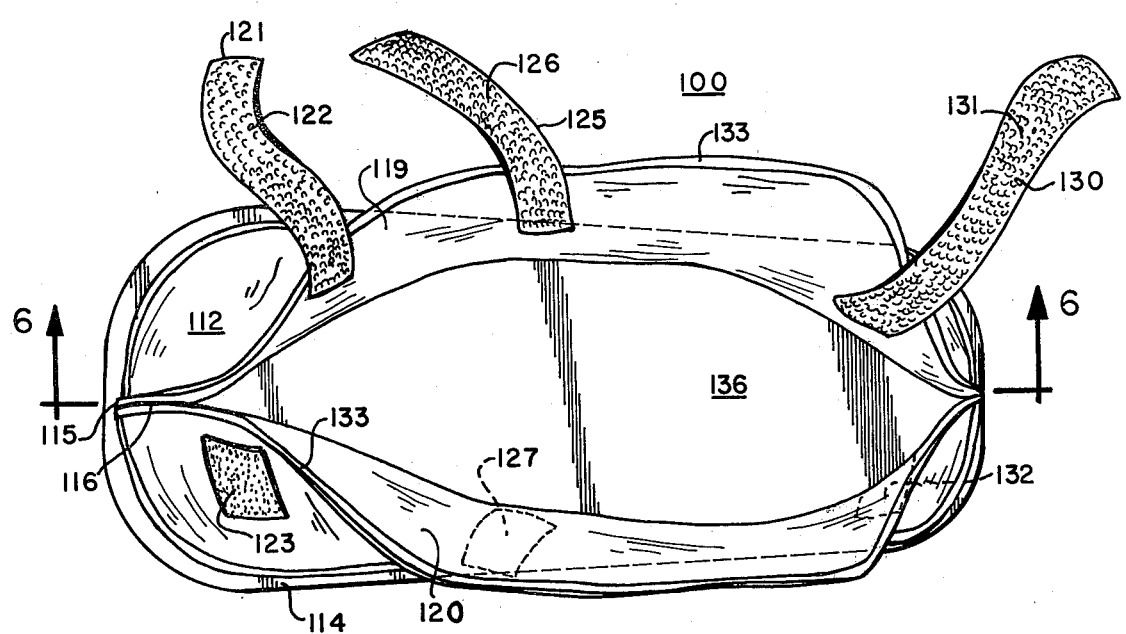
FIG. 5 is a top plan view of the shoe of FIG. 3.
Figure 6:
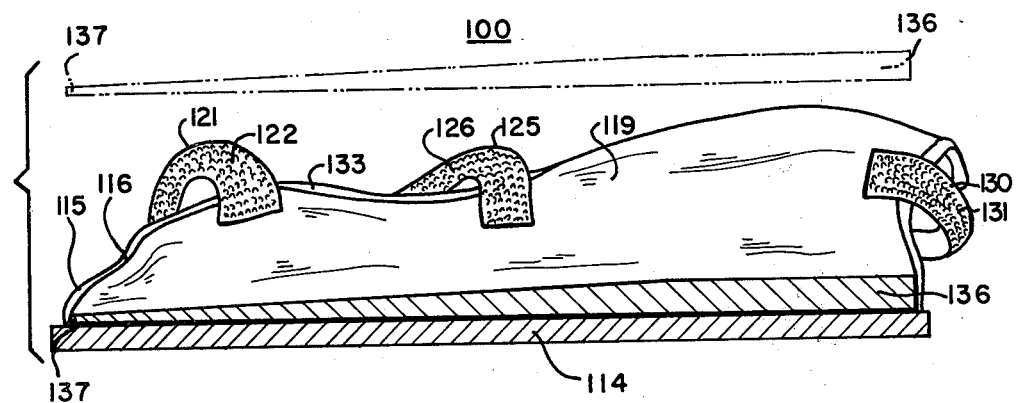
FIG. 6 is a vertical sectional view taken approximately on the line 6—6 of FIG. 5.

Referring now more particularly to FIGS. 3, 5 and 6 another embodiment of shoe 100 is illustrated which includes an upper 112 and a sole 114. The upper 112 is formed of two side halves 119 and 120 which are joined to the sole 114 by any suitable means such as lines of stitching (not shown) or a film of adhesive of well known type and which are joined together at the toe 115 to a point 116 by a line of stitching (not shown).

The halves 119 and 120 may be provided with strips of cloth edging 133 along their facing edges, a strap 121 is provided at toe 115 portion fastened to half 119 with a strip of thistle cloth 122 on one side for engagement with a complemental strip of thistle cloth 123 on half 120.

A second strap 125 is provided attached to half 119 over the top of the foot (not shown) with a strip of thistle cloth 126 on one side for engagement with a complemental strip of thistle cloth 127 on the half 120.

A third strap 130 is provided attached to half 119 at the rear of the foot (not shown) with a strip of thistle cloth 131 on one side for engagement with a complemental strip of thistle cloth 132 on half 120.

The sole 114 is of uniform thickness from end to end of the same material as sole 14 with a non slip pattern (not shown) on the bottom thereof. The sole 114 has an inner heel wedge 136 inside of the sole 114 and upper 112 adjacent thereto. The inner heel wedge 136 is of a tapered construction, from the rearmost portion shown in FIG. 3 and tapers gradually lengthwise until it terminates at a knife like edge 137 at the front most portion of the shoe 100.

Figure 4:
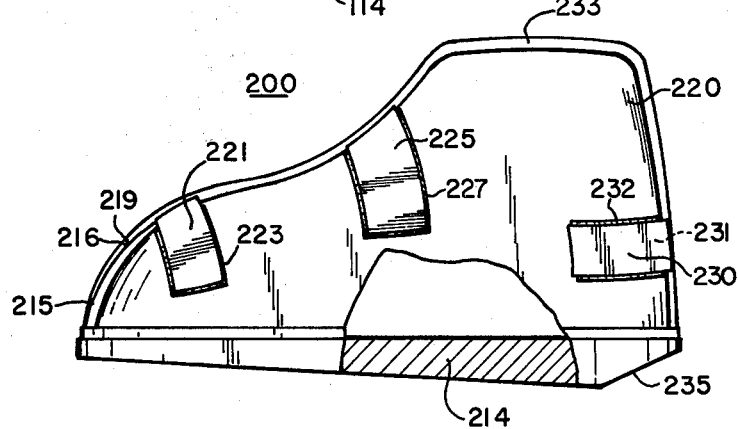
FIG. 4 is a side elevational view of still another embodiment of the shoe of the invention with a portion removed to show the internal construction.

Another embodiment of shoe 200 is shown in FIG. 4 which includes an upper 212 and a sole 214. The upper 212 is composed of side halves 219 and 220 which are secured to sole 214 by any suitable means such as lines of stitching (not shown) or a film of adhesive of well known type.

A front strap 221 is provided fastened to half 219 and with a strip of thistle cloth (not shown) on one side for engagement with a complemental strip of thistle cloth 223 on half 220. The halves 219 and 220 have strips of cloth edging 233 on their facing edges and are fastened toegether at the toe portion 215 to point 216 by lines of stiching (not shown).

A second strap 225 is provided fastened to half 219 with a strip of thistle cloth (not shown) on one side for engagement with a complemental strip of thistle cloth 227 on half 220.

A third strap 230 is provided attached to half 219 around the rear portion of the ankle (not shown) with a strip of thistle cloth (not shown) on one side for engagement with a complemental strip of thistle cloth 232 on upper half 220.

The sole 214 of the same material as soles 14 and 114 is of tapered construction from the rear to the front, with the rear being about one and one-half times as thick as the front, and with a rear beveled portion 235 adjacent the heel at an angle opposite to that of the rest of sole 214.

When it is desired to install the shoes 10, 100 or 200 the straps 21, 25, 30, 121, 125, 130, 221, 225 and 230 are respectively detached from their respective strips of thistle cloth 23, 27, 32, 123, 127, 132, 223, 227, and 232 on halves 20, 120, and 220. The cast 11 may then be inserted into shoes 10, 100 or 200 and the thistle cloth portions of straps 21, 25, 30, 121, 125, 130, 221, 225 and 230 engaged with the strips of thistle cloth 23, 27, 32, 123, 127, 132, 223, 227, and 232. The cast 11 is surrounded at the bottom, protected from the elements and the weight of the cast is supported evenly along the soles 14, 114 or 214, the straps accommodating different sizes of casts as desired.

It will thus be seen that shoes have been provided with which the objects of the invention are attained.

I claim:

1. A shoe to be worn over a cast which comprises
    an upper which is adapted to fit around the lower portion of a cast which has a toe and heel portion, the upper including
    a pair of side halves detachably secured around the cast by a plurality of straps,
    a sole attached to said upper,
    said upper side halves meeting at the front and back of said sole,
    a heel wedge portion associated with said sole which imparts a lift to the heel portion of the cast,
    said straps being attached to one of said upper halves,
    said straps comprising a rear strap horizontally disposed for restraining relative movement between the cast and the sole, and
    spaced forwardly disposed straps for restraining relative movement between the cast and the sole,
    said straps having strips of thistle cloth attached thereto for adjustable engagement with strips of complemental thistle cloth attached to said other of said halves.

2. A shoe to be worn over a cast as defined in claim 1 in which
    said heel wedge portion is interposed between said upper and said sole.

3. A shoe to be worn over a cast as defined in claim 1 in which
    said heel wedge portion is inside of said upper and directly bearing against said cast.

4. A shoe to be worn over a cast as defined in claim 1 in which
    said heel wedge portion is external to and a part of said sole.

* * * * *